US006656683B1

(12) United States Patent
Reuben et al.

(10) Patent No.: US 6,656,683 B1
(45) Date of Patent: Dec. 2, 2003

(54) LASER SCANNING CYTOLOGY WITH DIGITAL IMAGE CAPTURE

(75) Inventors: James M. Reuben, Houston, TX (US); Terry L. McCutcheon, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/610,042

(22) Filed: Jul. 5, 2000

(51) Int. Cl.$^7$ .................... C12Q 1/68; C12N 5/02; G06K 9/00; G06I 1/00
(52) U.S. Cl. .................... 435/6; 435/325; 382/133; 382/134; 345/418
(58) Field of Search .................... 435/6; 436/63, 436/64, 501, 500; 345/418, 972; 382/133, 134; 348/273

(56) References Cited

U.S. PATENT DOCUMENTS

| | | |
|---|---|---|
| 4,523,278 A | 6/1985 | Reinhardt et al. |
| 5,072,382 A | 12/1991 | Kamentsky |
| 5,235,522 A | 8/1993 | Bacus |
| 5,427,910 A | 6/1995 | Kamentsky et al. |
| 5,526,258 A | 6/1996 | Bacus |
| 5,587,833 A | 12/1996 | Kamentsky |
| 5,793,969 A | 8/1998 | Kamentsky et al. |
| 5,885,840 A | 3/1999 | Kamentsky et al. |
| 6,002,788 A | 12/1999 | Luther |
| 6,046,772 A * | 4/2000 | Howell ............ 348/273 |
| 6,078,681 A | 6/2000 | Silver |
| 6,151,405 A * | 11/2000 | Douglass et al. ......... 382/133 |
| 6,165,739 A | 12/2000 | Clatch |

FOREIGN PATENT DOCUMENTS

| | | |
|---|---|---|
| WO | WO 98/35223 | 8/1998 |
| WO | WO 9838490 | 9/1998 |
| WO | WO 9942809 | 8/1999 |
| WO | WO 99/45094 | 9/1999 |

OTHER PUBLICATIONS

Kamentsky et al., "Slide–Based Laser Scanning Cytometry", The International Academy of Cytology, vol. 41, No. 1, pp. 123–143 (1997).*
Kamentsky et al. Slide–Based Laser Scanning Cytometry. Acta Cytologica vol. 41, pp. 123–143, Feb. 1997.*
Compucyte Incorporation. CompuCyte product information and Sales. Cambridge, MA, 02139, pp. 1–3, Apr. 1999.*
Kamentsky et al. Slide–Based Laser Scanning Cytometry. Acta Cytologica vol. 41, pp. 123–143.*
Compucyte Incorporation. CompuCyte product information and Sales. Cambridge, MA, 02139, pp. 1–3.*
Park, Chan H. et al.; Tumor Cell–Selective Flow Cytometric Analysis for DNA Content and Cytokeratin Expression of Clinical Tumor Specimen by "Cross–gating"; Anticancer Research 14: pp. 29–36, 1994.
Gorczyca W Et Al., *Analysis of apoptosis in solid tumors by laser–scanning cytometry*, Mod Pathol, Nov. 1998, pp. 1052–1058, vol. 11, No. 11.

Rew Da Et Al., *Comparison of flow and laser scanning cytometry for the assay of cell proliferation in human solid tumor*, Cytometry, 1998, pp. 355–361, vol. 33, Wiley–Liss, Inc.
Kawamura K Et Al., *DNA ploidy analysis of urinary tract epithelial tumors by laser scanning cytometry*, Analytical & Quantitative Cytology & Histology, Feb. 2000, pp. 26–30, vol. 22, No. 1, The Int'l Academy of Cytology.
Clatch RJ Et Al., *Immunophenotypic analysis of hematologic malignancy by laser scanning cytometry*, Hematopathology, pp. 744–755, vol. 105, No. 6.
Kamentsky LA Et Al., *Methods for automatic multiparameter analysis of fluorescence in situ hybridized specimens with a laser scanning cytometer*, Cytometry, 1997, pp. 117–128, vol. 27, Wiley–Liss, Inc.
Kamentsky LA Et Al., *Microscope–based multiparameter laser scanning cytometer yielding data comparable to floe cytometry data*, Cytometry, 1991, pp. 381–387, vol. 12, Wiley–Liss, Inc.
Folberg R Et Al., *The morphologic characteristics of tumor blood vessels as a marker of tumor progression in primary human uveal melanoma*, Human Pathology, Nov. 1992, pp. 1298–1305, vol. 23, No. 11.
Clatch RJ Et Al., *Multiparameter analysis of DNA content & cytokeratin expression in breast carcinoma by laser scanning cytometry*, Arch Pathol Lab Med, Jun. 1997, pp. 585–592, vol. 121.
Schrock E Et Al., *Multicolor spectral karyotyping of human chromosomes*, Science, Jul. 26, 1996, pp. 494–497, vol. 273.
Clatch RJ Et Al., *Simplified immunophenotypic analysis by laser scanning cytometry*, Cytometry (Communications in Clinical Cytometry), 1998, pp. 3–16, vol. 34, Wiley–Liss, Inc.
Kamentsky LA Et Al., *Slide–based lase scanning cytometry*, Acta Cytologica, Jan.–Feb. 1997, pp. 123–143. vol. 41, No. 1, The Int'l Academy of Cytology.
Bedrossian C.W.M., *Special stains, the old and the new: the impact of immunocytochemistry in effusion cytology*, Diagnostic Cytopathology, 1998, pp. 141–149, vol. 18, No. 2, Wiley–Liss, Inc.
Strohmaier A–R Et Al., *Tomography of cells by confocal laser scanning microcopy and computer–assisted three–dimensional image reconstruction: localization of Cathepsin B in tumor cells penetrating collagen gels in vitro*, The Journal of Histochemistry & Cytochemistry, 1997, pp. 975–983, vol. 45, No. 7, The Histochemistry Society, Inc.

* cited by examiner

Primary Examiner—Kenneth R. Horlick
Assistant Examiner—Cynthia B. Wilder
(74) Attorney, Agent, or Firm—Fulbright & Jaworski L.L.P.

(57) ABSTRACT

The methods described herein are directed to subjecting a biological cell sample with multiple cell characteristics, such as DNA ploidy, immunophenotype or cellular morphology, to a laser-based interrogation with the penultimate step being creation of a digital image of the cell sample. This digital image greatly enhances the comprehensive analysis of the sample and facilitates diagnosis of the cell characteristics upon its creation in a digital format, which may also be captured in a tangible format such as a hard copy, either of which are suitable for transmission to a diagnostician, health care provider or patient.

45 Claims, 8 Drawing Sheets

CYTOLOGY AND PLOIDY ANALYSIS

PATIENT: Patient, Name - 34567    REFERRING PHYSICIAN: Physician Name
SPECIMEN: Voided Urine   COLLECTED: 11/30/98   RECEIVED: 12/07/98
ACCESSION NUMBER: NG98-12345

DIAGNOSIS:
Cellular changes consistent with Polyoma virus.
COMMENT:
Polyploid cell population consistent with viral cytopathic changes.

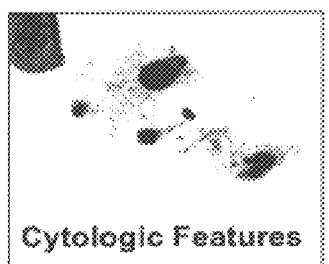
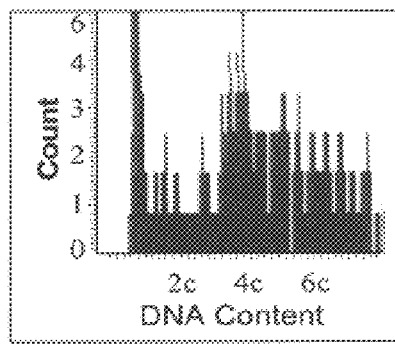

Longitudinal Analysis of Cytology & DNA Ploidy

| Cytology | | DNA Ploidy |
|---|---|---|
| Other | | Aneuploid >5c |
| TCC | | Tetraploid 4c |
| Dysplasia | | S-phase >2c |
| Atypia | | Hyperploid >2c |
| | | Diploid 2c |
| Negative | | Hypoploid <2c |

11/30/98

CYTOPATHOLOGIST      DATE

FIG. 1

CYTOLOGY AND PLOIDY ANALYSIS

PATIENT: Patient, Name - 34567   REFERRING PHYSICIAN: Physician Name
SPECIMEN: Urinary Bladder Washing   COLLECTED: 12/17/98   RECEIVED: 12/18/98
MDAC ACCESSION NUMBER: NG98-13579   SBCL ACCESSION NUMBER: SB98-13579

DIAGNOSIS:
TRANSITIONAL CELL CARCINOMA, GRADE 2.
COMMENT:
DNA ploidy analysis of cytokeratin-positive cells shows the majority (59.9%) of cells to be diploid with 13.2% having DNA content >5c.

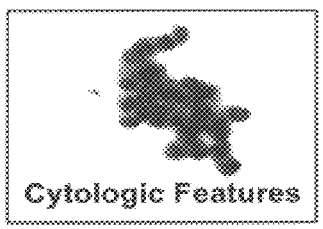
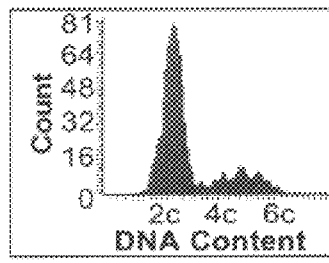
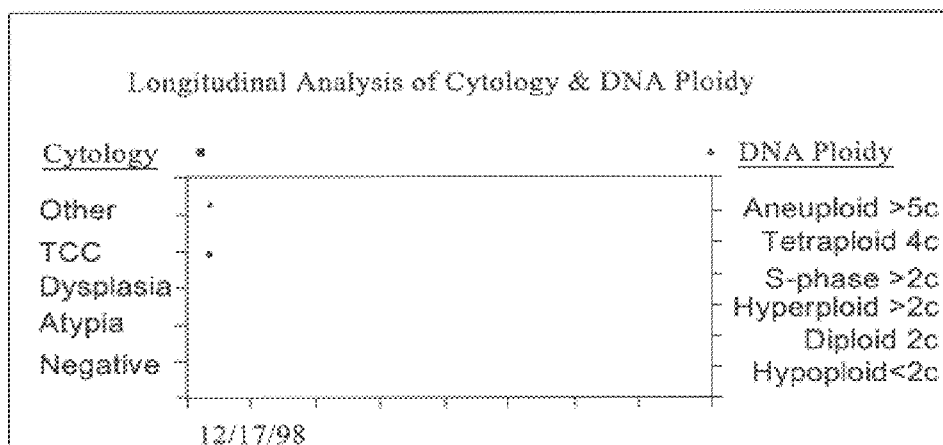

CYTOPATHOLOGIST     DATE

FIG. 2

CYTOLOGY AND PLOIDY ANALYSIS

PATIENT: Patient, Name - 000000    REFERRING PHYSICIAN: Doctor, Name, M.D.
SPECIMEN: Bladder Washing  COLLECTED: 03/10/00  RECEIVED: 03/13/00
ACCESSION NUMBER: NG00-0000 (LC00-00)

DIAGNOSIS:
TRANSITIONAL CELL CARCINOMA, HIGH GRADE (SEE COMMENT)
COMMENT:
Ploidy analysis of cytokeratin-positive cells reveals an aneuploid population with a proliferation index of 31.9% and 10.0% of cells with DNA content >5c. These findings support the above cytologic diagnosis.

Final Diagnostic Category
- Negative ☐    TCC ☒
- Atypia ☐      Other malig. ☐
- Suspicious ☐  Viral ☐

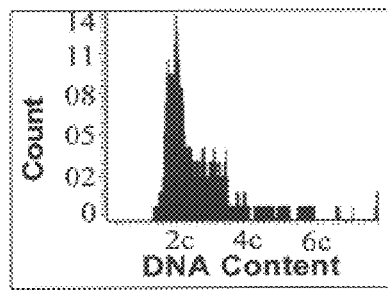

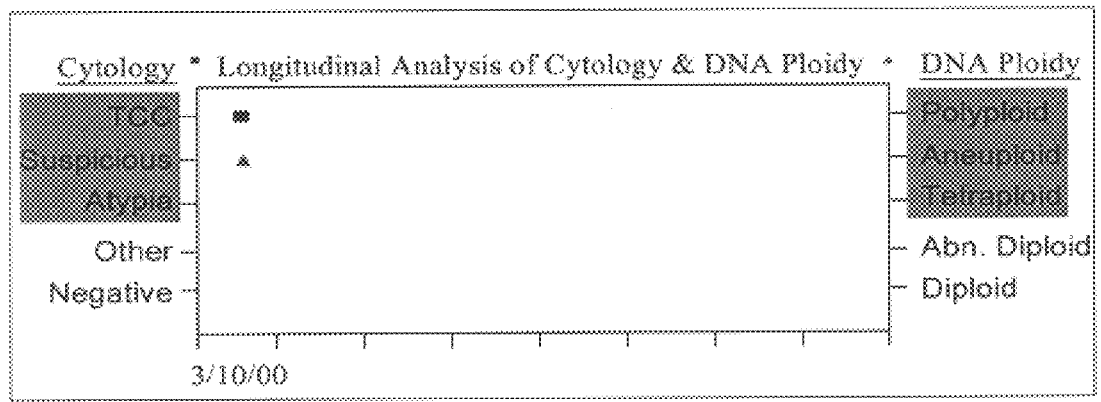

March 00, 0000
DATE

FIG. 3

CYTOLOGY AND PLOIDY ANALYSIS

PATIENT: Patient, Name - 000000    REFERRING PHYSICIAN: Physician Name, M.D.
SPECIMEN: Voided Urine  COLLECTED: 03/16/00  RECEIVED: 03/20/00
ACCESSION NUMBER: NG00-0000  (LC00-00)

---

DIAGNOSIS:
No malignant cells identified (see comment)

COMMENT:
Ploidy analysis of cytokeratin-positive cells reveals a diploid population with a proliferation index of 6.5% and 0% of cells with DNA content >5c. These findings are consistent with the above cytologic diagnosis.

Final Diagnostic Category
- Negative ☒      TCC ☐
- Atypia ☐        Other malig. ☐
- Suspicious ☐    Viral ☐

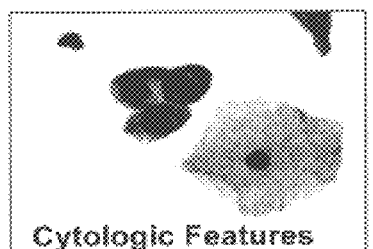
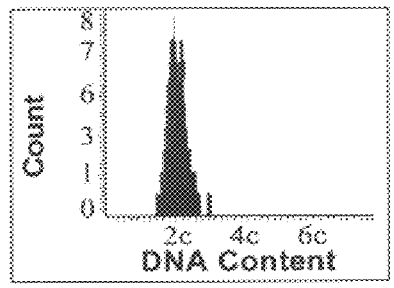

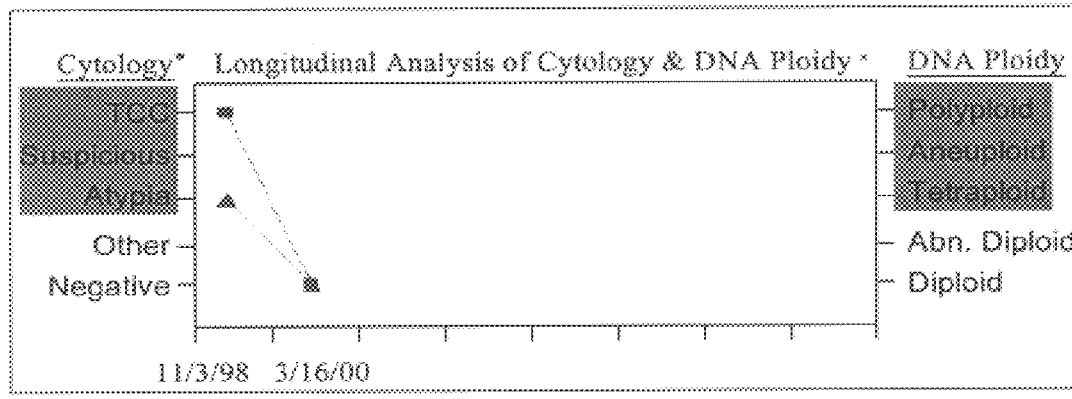

March 00, 0000
DATE

FIG. 4

LASER SCANNING CYTOLOGY WITH DIGITAL IMAGE CAPTURE

BACKGROUND OF THE INVENTION

1. Field of the Invention

The invention relates generally to the field of cellular biology. More particularly it concerns the use of a laser scanning cytometer with a digital camera to capture an image of cells in a sample for diagnosis of cell characteristics. More specifically, it relates to diagnostics regarding cancerous cells.

2. Description of Related Art

Pre-malignant and malignant cellular transformation is associated with changes in cell morphology and in DNA content. For early cell transformations in the absence of apparent aberrant cell morphology (a negative cytology), changes in DNA content, detected by ploidy analysis, are critical in establishing the diagnosis. DNA ploidy analysis is performed using a Laser Scanning Cytometer (LSC™). The LSC is laser based technology that combines immunofluorescence, cell morphology and DNA ploidy analysis to enhance the sensitivity and specificity for detecting malignant cells. This method is capable of not only measuring DNA ploidy but identifying individual cell types based on their immunophenotype. The immunophenotype of epithelial cells from urine is determined by staining the cell cytoplasm for the presence of cytokeratin. By combining the immunophenotype with the DNA ploidy pattern, the pathologist can now identify epithelial cells that are aneuploid, a profile consistent with specific cancer cells.

Previous methods using laser scanning cytology, such as described in U.S. Pat. No. 5,793,969, U.S. Pat. No. 5,885,840, U.S. Pat. No. 5,427,910 and Kawamura et al. (2000) are directed to LSC methods in which the images are visualized by a monitor display or by means of a CCD camera, and stored in a computer disk file. This arrangement of equipment is most useful if a cytopathologist is on-site and furthermore present during analysis to visualize the image on the monitor and make the diagnosis at that point in time. The image itself is additionally not transferable to others related to its diagnosis. Thus, a method to remove this constraint for analysis and moreover provide a tangible means to retain the data is lacking in the art.

SUMMARY OF THE INVENTION

The present invention described herein overcomes significant limitations in the art of laser scanning cytology methods. The inventors describe herein methods to record data from a biological sample containing a cell by using a digital camera. In specific embodiments, the capture of the image in a digital form facilitates examination of the data in a format conducive to a more thorough analysis and diagnosis. The inventors envision that the LSC methods described herein permit a more efficient and convenient analysis of immunophenotype, DNA ploidy and cell morphology in pursuit of diagnosis of cell characteristics, such as those related to cancer. In further specific embodiments, the analysis of the cell characteristics from a urine sample using the LSC methods of the present invention provide diagnosis for the presence of transitional cell carcinoma.

In an embodiment of the present invention there is a method for recording cell sample data comprising providing a sample containing a cell; subjecting said sample to a laser-based interrogation; and capturing a digital image of one or more cell characteristics. In a specific embodiment, the digital image is directly captured. In another specific embodiment, the method further comprises analyzing one or more cell characteristics. In an additional specific embodiment, the method further comprises analyzing one or more cell characteristics by fluorescent in situ hybridization. In a further embodiment, the one or more cell characteristics are selected from the group consisting of immunophenotype, DNA ploidy, cell morphology, nuclear fragments and subcellular fragments. In a specific embodiment, one or more cell characteristics comprises immunophenotype, DNA ploidy, cell morphology, nuclear fragments and subcellular fragments. In an additional embodiment, the cell is selected from the group consisting of an animal cell, a plant cell and a prokaryotic cell. In another specific embodiment, the animal cell is selected from the group consisting of a cancer cell, an epithelial cell, a bone marrow cell, a red blood cell, a white blood cell, a muscle cell, a bone cell, a connective tissue cell, a nerve cell and a brain cell. In another embodiment, the cell is a cancer cell. In a further specific embodiment, the method further comprises the step of preparing a cell sample. In a specific embodiment, the preparation step comprises processing of a sample, wherein said sample processing is selected from the group consisting of concentration, dilution, microscope analysis preparation, applying a stain or marker agent, or a combination thereof. In an additional specific embodiment, the sample is selected from the group consisting of urine, blood, sputum, feces, saliva, marrow, touch preps of surgical specimens, fine needle aspirates and cellular body fluid.

In an additional embodiment of the present invention the method further comprises capturing a video image, a color image or a black and white image of said cell sample. In another specific embodiment, the marker agent is selected from the group consisting of cytokeratin, propidium iodide, CD19, CD34, CD3, annexin V, and a combination thereof. In another specific embodiment the DNA ploidy of said cell is aneuploid. In another specific embodiment, one or more cell characteristics are analyzed from the same said digital image. In a further specific embodiment the immunophenotype is determined by applying a marker agent. In another specific embodiment, the marker agent is selected from the group consisting of cytokeratin, propidium iodide, CD19, CD34, CD3, annexin V, and a combination thereof. In an additional specific embodiment, the immunophenotype is determined by applying multiple marker agents.

In another object of the present invention there is a method of diagnosing cancer comprising providing a sample containing a cell; subjecting said sample to a laser-based interrogation; capturing a digital image of one or more cell characteristics; and identifying aneuploidy based on said one or more cell characteristics.

In an additional object of the present invention there is a laser-based cell analyzer comprising a laser; a first camera port; a second camera port; and a third camera port, wherein said cell analyzer facilitates determination of cell type. In a specific embodiment, the cell analyzer further comprises a digital camera attached to one camera port. In another specific embodiment, the cell analyzer further comprises a color camera attached to one camera port. In an additional embodiment, the cell analyzer further comprises a black and white camera attached to one camera port.

In another object of the present invention there is a laser-based cell analyzer system comprising a black and white camera attached to a first camera port; a color camera attached to a second camera port; and a digital camera attached to a third camera port. In a specific embodiment, the cell analyzer system further comprises a computer. In an additional embodiment, the cell analyzer system further comprises a printer.

In an additional object of the present invention there is a method for creating a cell data record comprising subjecting a cell to laser interrogation; and recording in a tangible medium one or more cell characteristics in a digital format.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 illustrates an example of a patient test report using an embodiment of a LSC with a video camera. Less detail is observed with regard to cellular matter.

FIG. 2 illustrates another example of a patient test report using an embodiment of a LSC with a video camera.

FIG. 3 illustrates an example of a patient test report using the preferred embodiment of a LSC with a digital camera.

FIG. 4 depicts an additional example of a patient test report generated with the preferred embodiment of a LSC with a digital camera.

DESCRIPTION OF ILLUSTRATIVE EMBODIMENTS

Figure 5:
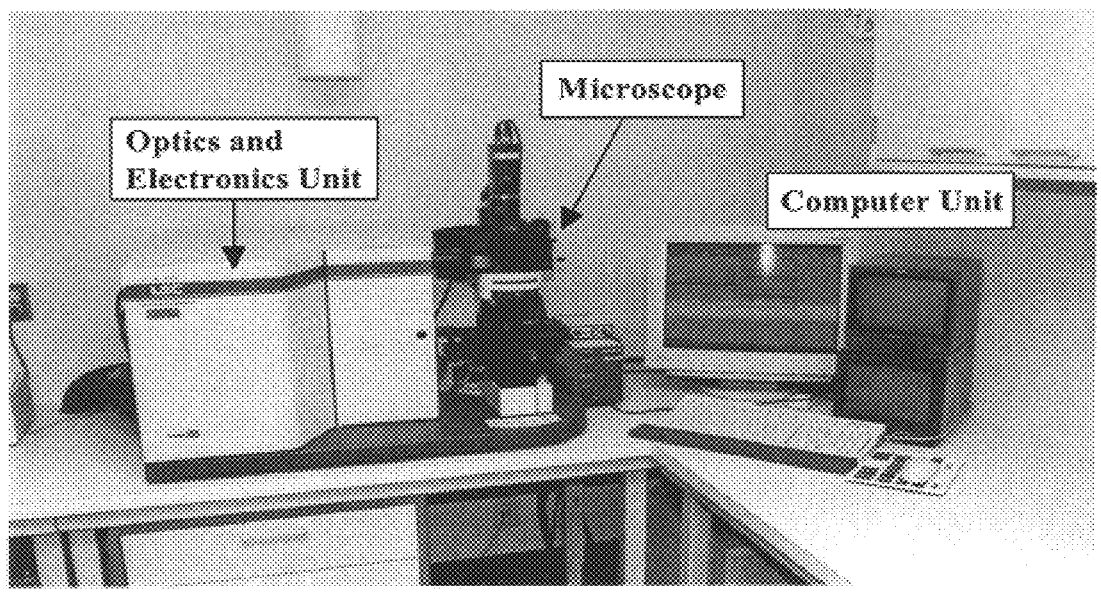
FIG. 5 depicts an embodiment of a laser scanning cytometry (LSC) system.

The present invention describes methods and compositions directed to using a laser scanning cytometer with a digital camera to obtain in a tangible form or medium a digitized version of a cell sample. The inventors envision the use of such a device and methods to use it for the purpose of analyzing cell characteristics such as immunophenotype, DNA ploidy and cell morphology. The information is stored in a digitized manner and can be retrieved, transmitted, and reproduced. This allows the review and assimilation of the data on morphology and DNA ploidy for comprehensive interpretation and digital transmission of the data and interpretation. The method is useful for the detection of DNA ploidy and phenotype of any cellular material or body fluid. In a specific embodiment the present invention is directed towards analysis of DNA ploidy in epithelial cells of a urine sample.

I. Definitions

The term "aneuploid" as used herein is defined as an abnormal number of chromosomes.

The term "capture" as used herein is defined as the attainment, acquisition or retrieval of information.

The term "cell morphology" as used herein is defined as the collection of physical characteristics of a particular cell.

The term "cell sample" as used herein is defined as a sample obtained from an organism, wherein said sample derives from but is not limited to urine, bone marrow, blood, lymph nodes, touch preps of surgical specimens, and a cellular body fluid. The sample may contain whole cells, cellular fragments, nuclear fragments, or combinations thereof.

The term "DNA ploidy" as used herein is defined as the number of copies of a chromosome set of a cell.

The term "euploid" as used herein is defined as a normal number of chromosomes.

The term "immunophenotype" as used herein is defined as the classification of a cell into a group based on its ability to test positive for a particular stain or marker agent.

II. The Present Invention

The present invention provides methods and compositions to record cell sample data utilizing a LSC with a digital camera. The digitized image of the cell sample is analyzed for identification of cell characteristics using DNA ploidy, immunophenotype and cell morphology. In a specific embodiment, a stain or marker agent such as cytokeratin is useful for identification of a particular classification of a cell. In other specific embodiments, DNA ploidy is analyzed for aberrant status of DNA ploidy, such as aneuploidy. The present invention offers improvements over known testing methods. The LSC instrument is more accurate because it is capable of analyzing a large quantity of intact cells (both nucleus and cytoplasm) and subsequently renders greater accuracy in testing based on statistical sampling. This is because LSC analyzes >500 cells/slide, as compared to image analysis, which analyzes typically 50–100 cells/slide.

The LSC methods described herein also permit improved specificity because the LSC methodology allows application of multiple marker agents, which facilitates enhanced specificity in testing. For example, for urine analysis up to 4 markers (including propidium iodide for DNA ploidy and cytokeratin for cells of epithelial origin) may be utilized. Furthermore, the LSC methodology includes production of a histogram which provides valuable information in helping to differentiate carcinoma from atypical cells (e.g., virally-infected cells). Finally, the ability of the LSC of the present invention to analyze intact cells, in contrast to other methods which analyze mitochondria or naked nuclei only, facilitates the diagnosis of examining an intact cell of known morphology and lineage.

An important addition to known methodologies of laser scanning cytology as described herein is the novel addition of a digital camera (compare FIGS. 1 and 2 with FIGS. 3, 4 and 5). In FIGS. 1 and 2 utilizing a video camera, less detail is observed with regard to cellular matter. In FIGS. 3 and 4, more detail is observed. The added advantages include: (1) computerized transmission of sharp digital images taken of cellular content (specimens) which are analyzed for the detection of malignant and pre-malignant cells; (2) ease in storage and record keeping; (3) graphic evidence of positive results; and (4) a state-of-the-art report presentation which also allows pathologists, diagnosticians, health care providers, medical insurance providers and patients to see the cells that were analyzed to establish the diagnosis.

Accordingly, it is an object of the present invention to provide a means for multiple simultaneous review of encoded information obtained from the slide analysis procedures of a microscope slide, including the manner in which the slide analysis was conducted and optionally including stored images of the slide. The present invention comprises a method for scanning a cell sample for analysis, multiple times, with different examination parameters with results of the multiple scannings being merged into a single profile of scanning results for individual cells in the sample and said method comprising the steps of:

a) utilizing scanning means to examine the cell sample and determine and record the position of individual cells relative to the scanning means, b) using the recorded cell positions of the individual cells from each of the multiple examinations as a key to merge results obtained for individual cells having positions within predetermined deviations values. It is preferred that the key also include positions outside predetermined overlapping distance values from adjacent cells.

c) utilizing the addition of the digital camera to capture the cell morphology, immunophenotype and DNA ploidy pattern in much greater and finer detail and to store the information for subsequent transmission, retrieval and pathology review, and record reproduction.

In a specific embodiment of the present invention, the LSC can be used to record the exact position of each cell along with other features. In this embodiment, a specimen is stained with both Argon ion excited dyes (i.e., Propidium Iodide) and red Helium Neon excited dyes that will not be excited by Argon ion laser emission. The specimen is assayed twice, once for each dye, and the results are merged using the position of each cell as the merge key yielding non interfering constituent measurement data.

An object of the present invention is to provide a means for review at two or more networked remotely located microscope sites linked to computer encoder-terminals. It is yet another object of the present invention to provide network capability at the terminal sites, for correlating slide information together with patient history and/or together with comparative observation information to render a comprehensive pathology review as well as to resolve any possible ambiguities in interpretation. Another object of the present invention is to provide automatic location and review of the flagged slide specimen view sites. An additional object of the present invention is to provide report retrieval and generation for patient records.

In a preferred embodiment, the present invention provides the LSC as laser based technology that combines immunofluorescence, cell morphology and DNA ploidy analysis to enhance the sensitivity and specificity for detecting malignant cells, which includes capturing these characteristics by digital means, such as a digital camera.

III. Cell Samples

The cell samples to be subjected to a laser-based interrogation are, in an object of the present invention, from a patient with an unknown or uncertain medical condition or whose medical condition is known but means of therapy remains to be determined. The sample for the present invention is directed to any cellular material including but not limited to urine, bone marrow, blood, touch preps of surgical specimens, fine needle aspirates and all cellular body fluids. Samples, as described herein, include body fluid comprising cells.

Touch prep specimens are generated by smearing or pressing onto a slide, applying pressure to the tissue, and fixing in ethanol under cool temperatures. In a specific embodiment the tissue is extracted surgically and smeared onto a glass slide by applying relatively weak pressure to tumor tissue and relatively strong pressure to normal tissue, followed by fixing in about 100% ethanol for approximately 10 minutes at about 4° C. In another specific embodiment, the samples to be analyzed by methods of the present invention are originally frozen in liquid nitrogen and stored at about −80° C.

In a specific embodiment the sample to be analyzed can contain primarily a cancer cell, an epithelial cell, a bone marrow cell, a red blood cell, a white blood cell, a muscle cell, a bone cell, a connective tissue cell, a nerve cell and a brain cell. In a preferred embodiment the cell is a cancer cell. In a more preferred embodiment the cancer cell is from a transitional cell carcinoma.

Specimens, or samples, of a cellular body fluid or material are received and concentrated and/or diluted, depending on the source. In a specific embodiment the samples are further processed or prepared. For example, cell suspensions may be purified by standard techniques including ficoll-hypaque density centrifugation. Although it is preferred to analyze intact cells, in one aspect of the invention fragments of cells or cell organelles are examined. For instance, in a specific embodiment red blood cells are lysed by salt exposure, such as by ammonium chloride. Microscopic slides are prepared using the concentrated or processed specimen to optimize cellular content and, in a preferred embodiment, are stained with propidium iodide for DNA content and with stains or markers for additional cell characteristics such as cytokeratin, CD19, CD34, CD3, annexin V, and a combination thereof.

Specific subtypes of cancers which are detected with anti-cytokeratin antibodies include adenocarcinomas, such as is found in the pancreas; gallbladder; lung; cervix; cholangiocarcinomas, such as is found in the liver; ductal or lobular carcinoma of breast; carcinoma of ovary; transitional cell carcinoma of bladder; and mesothelioma. Occasionally staining of blood vessel walls, particularly in endothelial cells, may be observed.

The processed or stained slides are scanned using the Laser Scanning Cytometer (LSC) instrument for the purpose of measuring DNA ploidy and identifying abnormal cell types based on immunophenotype. In an object of the present invention the cell characteristics are observed simultaneously through a microscope or monitor. Multiple photographs (in a specific embodiment, approximately five) of the cellular content are taken using a digital camera, with particular emphasis on any abnormal or atypical cells. In addition, a histogram is produced from the analysis of the cellular DNA content. A cytopathologist, or one of skill in the art, reviews the digital image and interprets DNA ploidy and cell types, assimilates these results with data on morphology, and renders a comprehensive report based on that complex and informative image.

IV. Cell Characteristics

In a specific embodiment one or more cell characteristics are examined by methods of the present invention including DNA ploidy, immunophenotype, and cellular morphology.
DNA Ploidy The number of copies of a chromosome set of a cell are its DNA ploidy. Aneuploid cells contain an abnormal number of chromosomes, whether there are too few or too many, and euploid cells have a normal number of chromosomes. Extra chromosomes may lead to unbalanced gene expression, whereas loss of chromosomes may lead to loss of critically important genes or DNA structures. However, the presence of a euploidic state of the chromosomes does not preclude a cell from containing a genetic change related to cancer. In a specific embodiment structural rearrangements of chromosomes are present in addition to numerical alterations, and these rearrangements may be detected by the methods of the present invention. The rearrangements may include translocations, deletions or inversions. In a specific embodiment the rearrangements are detected by banding of stained chromosomes, which detects subtle chromosomal structural changes. Banding of stained chromosomes comprises longitudinal cross staining, which is constant for each chromosome pair, although it varies between chromosomes. Banding patterns for all of the human chromosomes are located in many textbooks and references known in the art, including *The Biological Basis of Cancer* (McKinnell et al., 1998). Methods well known in the art relate characterization of each chromosome with its own distinct color by labeling with a combination of fluorescent dyes, permitting microscopic characterization of each chromosome (Schrock et al., 1996).

In a preferred embodiment, DNA ploidy analysis is made in the context of comparison to normal, non-cancerous tissue of the same type.

Immunophenotype

Characteristic molecules synthesized by tumors are often presented on the surface of tumor cells. Alternatively, cellular hallmarks such as DNA or nucleic acid, internal to the cell surface, may be stained with specific compounds. Stains, marker agents or antibodies directed to these surface molecules facilitate characterization of a cell being cancerous or alternatively characterization of a cell type. Stains or marker agents include cytokeratin, propidium iodide, hematoxylin-eosin, fluorescein-conjugated lectin, Ulex europaeus I (F-UEAI) counterstained with Harris hematoxylin, periodic acid-Schiff (PAS), bromodeoxyuridine, cathepsin B, acridine orange and monoclonal antibodies purified as well as conjugated with a fluorochrome. Other stains are known in the art and may be summarized in references such as Bedrossian (1998).

The stains or markers may be visualized directly by fluorescence, light, color, radiation, etc., or they may be visualized indirectly, such as with antibody binding or secondary staining, such as with counterstaining. In a specific embodiment, cells are visualized with anti-cytokeratin antibodies which bind to cytokeratin-expressing cells. In other embodiments monoclonal antibodies are conjugated to fluorescein isothiocyanage (FITC), phycoerythrin or PE/Cyanin 5.

Cellular Morphology

The cell nucleus may be stained by specific stains, such as propidium iodide. In a specific embodiment propidium iodide at 50 mg/mL in a solution containing 0.1% RNAase is utilized. The propidium iodide, in a specific embodiment, is excited by a 488 nm wavelength argon-ion laser, and the red fluorescence emission is measured by appropriately filtered photomultiplier tubes. Specific tubes may be selected by one of skill in the art. In another specific embodiment, cellular noise such as nuclear debris or overlapping nuclei are gated out by special statistical filters.

Differences between apical and basal surfaces may be determined. Topography (morphology) of a specific cell may be smooth, asymmetrical, symmetrical, uneven, or marked with small or large pocks. Extensions on cells such as filopodia may be visualized.

Fluorescence in situ Hybridization

In an embodiment of the present invention, fluorescence in situ hybridization (FISH) is utilized to analyze a cell characteristic. In this technique a fluorescently labeled nucleic acid probe preferentially hybridizes with a complementary nucleic acid sequence, or target nucleic acid, on one or more chromosomes in a cell. The target nucleic acid may be unique or repetitive, and in a preferred embodiment it is used to distinguish one or more specific chromosomes. The fluorescent label is detected by the LSC.

In specific embodiments aneuploidy is determined by counting spots per cell using a DNA probe specific to one chromosome. Translocations and rearrangements are determined by using DNA probes covering the translocation or rearrangement and a nearby or adjacent sequence and determining whether the fluorescence regions from each sequence are separated or concentric. Amplification, deletion and point mutations are determined by quantifying the fluorescence from fluorescent regions using FISH for a specific target nucleotide sequence.

V. Laser Scanning Cytometry

In laser scanning cytometry (LSC), a combination of flow cytometric techniques of fluorochromatic cell sample excitation and microscopic analysis with sample presentation (see Kamentsky et al., 1990; Kamentsky et al., 1991). A laser beam scans a sample on a fixed medium such as a slide, and the position of the cells and each cell figures are simultaneously determined and recorded. Details regarding methods to use a LSC are well known in references in the art, such as Clatch et al. (1998); U.S. Pat. Nos. 5,427,910; 5,793,969; and 5, 885,840, each herein incorporated by reference.

The software for LSC allows multiple different geographic regions for automatic scanning of a sample. The data obtained from the analysis are collected and stored within a computer file. Values for each of three fluorescence channels, including green, orange and long red, are obtained. A scattergram of y position versus x position maps the location of the cells on a slide.

VI. Laser Scanning Cytometer

The LSC, as illustrated in an overview form (FIG. 5), is utilized to quantify cell constituents using fluorescence to measure scatter as well as fluorescence. In a specific embodiment a CompuCyte (Cambridge, Mass.) laser scanning cytometer is used. The LSC automatically measures fluorescence at multiple wavelengths of cells that have been treated with one or more fluorescent dyes in order to rapidly assay multiple cellular constituents. Fluorescence and scatter result from interpretation of the cells with a laser beam comparable in spot size to the cell. The laser optics is designed to produce a large depth of field with nearly collimated excitation to achieve accurate constituent measurements independent of cell position in the slide focus. Wavelength band pass filters are used to isolate the fluorescence to each of the multiple photomultipliers.

Cells are measured and retained on a solid support. In a specific embodiment the solid support is a slide, and the slide position and laser beam are moved under computer control to excite the cells. Since the position of the slide and laser beam is known to the computer, cell position on the slide is a measurement feature. Interactions of each cell and the laser beam are measured and recorded many times in a two-dimensional pattern and features computed from these inter-actions are derived.

Figure 6:
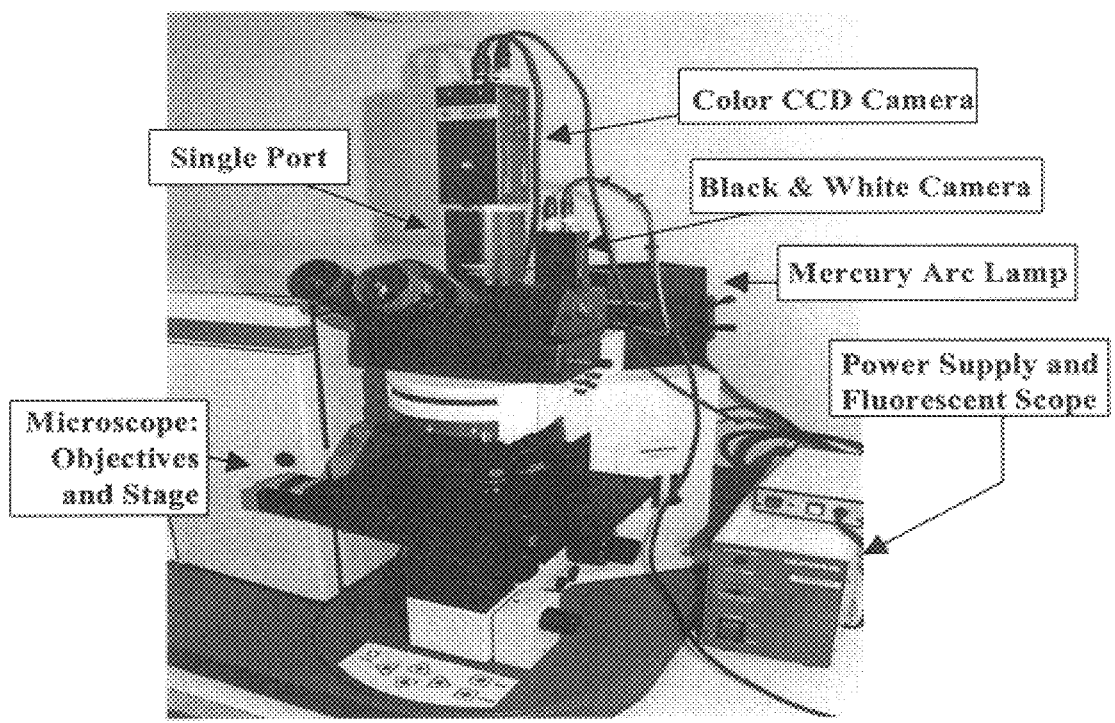
FIG. 6 illustrates a close-up view of the laser scanning cytometer (LSC).
Figure 7:
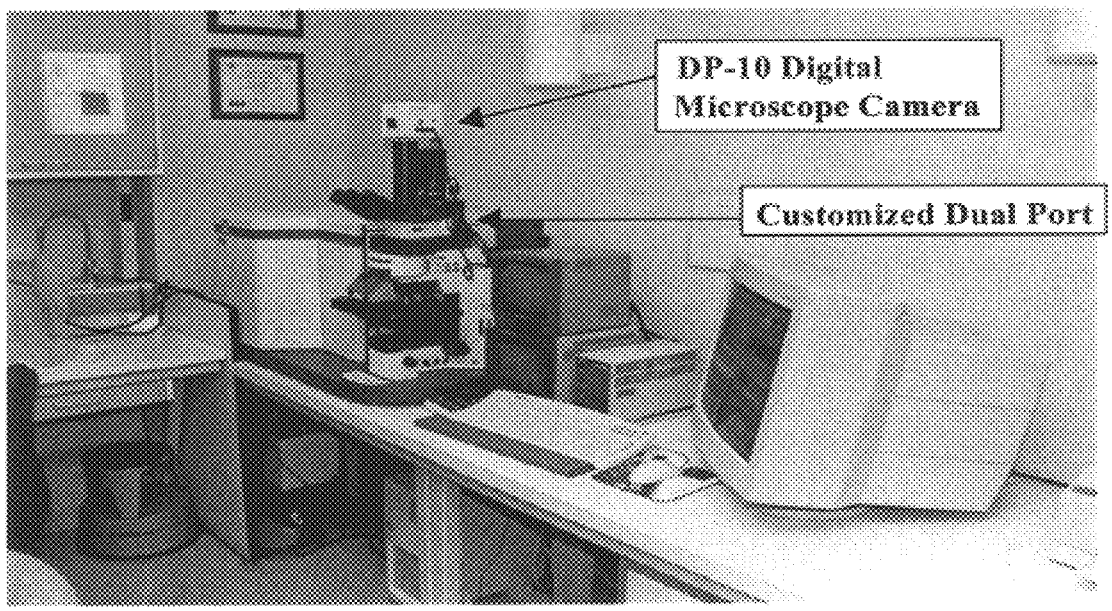
FIG. 7 depicts a laser scanning cytometer with customized Olympus dual port and DP-10 digital microscope camera.

In accordance with the objects of the present invention, specific embodiments are described as follows and as shown in FIGS. 6 and 7. The beams from the Argon ion and Helium Neon laser are combined at a dichroic mirror and steered to a second dichroic mirror designed to reflect the laser wavelengths and to transmit other wavelengths. The output of each laser is controlled by the LSC computer. After passing through a scan lens, in a specific embodiment, the beam enters the epi-illumination port of a standard Olympus BX50 microscope and is imaged by the objective lens onto the focal plane at the specimen, producing a 10 mu diameter spot over 685 mu using a 10 times objective, a 5 mu diameter spot over a 342 mu using a 20 times objective, or a 2.5 mu spot over a 171 mu using a 40 times objective.

The specimen is mounted in a holder on the stage of a computer controlled stepper motor stage equipped with absolute position sensors. The assembly's position is computer controlled to move outside the microscope's bright field source so that the microscope's bright field source can be used for viewing objects through the eyepiece, the CCD camera, or with the addition of a customized port, through a digital camera. Fluorescent energy is collected by the objective lens, reflected by a partially silvered mirror to allow a CCD camera to image cells, and steered through the scan lens and to the scanning mirror. It then passes through a series of dichroic mirrors and optical interference filters to up to 4 photomultipliers, each detecting a certain fluorescence wavelength range. Four sensor signals can be simultaneously digitized at 625,000 Hz and the digital values stored directly in banks of memory in a computer such as a PC computer.

A. Customized Olympus Port

Figures 8, 9:
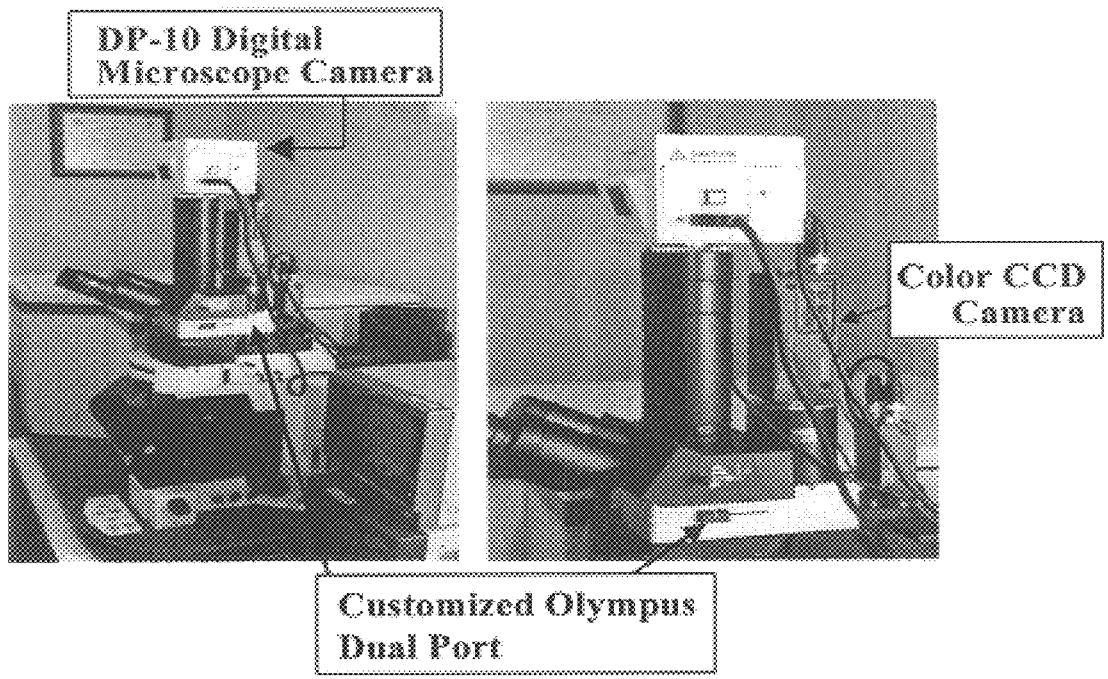
FIG. 8 illustrates the customized Olympus dual port and DP-10 digital microscope camera.
FIG. 9 shows another view of the customized Olympus dual port and DP-10 digital microscope camera.

In a specific embodiment a customized Olympus (Minneapolis, Minn.) dual head port is mounted on the front of the LSC, as shown in FIGS. 8 and 9. The addition of the dual port accommodates: (1) the original CCD camera and (2) the new Olympus digital camera assembly. The dual port allows enhancement of the color image without sacrificing the use of the black and white camera. In addition, the configuration allows the ability to monitor the entire scan and to capture digital images without having to change software programs.

B. DP-10 Digital Microscope Camera

The digital microscope camera is utilized to convert an analog image on a computer monitor into a digital visualizable form that can then be stored, transmitted and reviewed, and used in conjunction with other morphological data to render a comprehensive consultation for pathology specimens. In a specific embodiment an Olympus (Minneapolis, Minn.)DP-10 digital microscope camera is used, although the use of any digital camera is within the scope of the invention (FIGS. 8 and 9). The DP-10 digital camera sets a standard for high quality digital photomicrography and incorporates features including direct video output for viewing specimens on a standard analog video monitor; TIFF image storage for capturing images without any data compression; direct-to-CCD imaging design requires no additional lenses; high resolution color display provides greater precision and ease of fine focusing on low magnification specimens; and progressive-scan CCD produces high-resolution digital images. In a specific embodiment an Olympus DP-11 digital camera is used.

VII. Digital Image Analysis

In a preferred embodiment the image of the sample cells is captured, transmitted or applied by any method in a digital form. In a more preferred embodiment a digital camera is utilized to convert an analog image on a computer monitor into a digital visualizable form. The digital form may be stored on a computer hard drive and/or is stored on a disk, such as a floppy disk, a compact disk, a zip disk or other storage means. This facilitates the ease of one of skill in the art to make a diagnosis of the cell pathology but advantageously allows a diagnosis to be rendered without having to be at the machine or equipment itself. Thus, a digital image may be transmitted off-site from the LSC and a diagnosis is made separate in space and time from the subjection of the sample to the LSC. The secured transmission may be through the internet or world wide web, or it may be on a disk or hardcopy. In a specific embodiment a hard copy is created of the digital image and distributed to a pathologist, diagnostician, health care professional, medical insurance provider, or patient.

VIII. Classification of Cancer

Surface markers, such as antigens present in a cellular envelope or membrane, are included as prognostic factors in the analysis of potentially cancerous cells. Examples include CDI9, CD34, CD3 and annexin V. In a specific embodiment transitional cell carcinoma, which may derive from epithelial cells in the bladder, is diagnosed using methods of the present invention through utilization of an epithelial cell-specific marker such as cytokeratin. Other cancer cell-specific markers are well known in the art (for example, see Bedrossian (1998)). In other embodiments other cancer cell types are diagnosed by methods of the present invention using surface markers specific to a particular type of cancer.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Method for Laser Scanning Cytometry Analysis

Specimens of approximately 50–100 milliliters (ml) of urine are received and concentrated. Microscopic slides are prepared using the concentrated specimen, to optimize cellular content, and are stained for DNA content and cytoplasmic characteristics using propidium iodide and cytokeratin, respectively. The processed and stained slides are scanned using the Laser Scanning Cytometer (LSC) instrument for the purpose of measuring DNA ploidy and identifying abnormal cell types based on immunophenotype. Approximately five photographs of the cellular content are taken using a digital camera, with particular emphasis on any abnormal or atypical cells. In addition, a histogram is produced from the analysis of the cellular DNA content. Review and interpretation is performed by a cytopathologist, who receives the results on DNA ploidy and cell types, assimilates these results with data on morphology, and renders a comprehensive report.

Example 2

Urocytology/DNA Ploidy Analysis

Analysis of DNA content is a useful laboratory indicator of prognosis for many tumors including transitional cell carcinoma (TCC). An abnormality in the DNA content of cells, called aneuploidy, is commonly associated with the chromosomal abnormalities found in malignant cells. When cells are labeled with fluorochromes that bind specifically and proportionately to the amount of cellular DNA, the signal obtained from each cell relates directly to the amount of DNA contained within its nucleus. Analysis of this information provides a fractional means of detecting cell populations with abnormal DNA content (euploid populations) and also permits the measurement of the fraction of cells in the various phases of the cell cycle.

Moreover, the lineage of the cell of interest can be established by incubating the cells with reagents that are capable of identifying unique lineage-specific surface or cytoplasmic antigens. To identify epithelial cells in the cell pellets of urine specimens, the sample is reacted with FITC-conjugated anti-cytokeratin (anti-CK) antibody that will preferentially bind to epithelial cells. Therefore, the histograms gated only on FITC positive cells are enriched for epithelial cells relative to other stromal and lymphoid cells. Furthermore, the DNA content of these epithelial cells can be generated based on the reactivity of PI with the nucleus of the epithelial cells.

As part of an official study, twenty-two specimens were split and run in parallel using the LSC and Image Analysis. Among the first 11 samples, one case of metastatic serous cancer was identified using the LSC, but missed using the Image Analysis.

Example 3

Equipment for LSC Methods

The following equipment may be used to practice the methods of the invention: Laser Scanning Cytometer, cytospin, vortex, micropipets, rotator, centrifuge, computer, printer and digital camera. In preferred embodiments the computer is a Compaq DeskPro, the color printer is a Hewlett Packard 2000C and the digital camera is an Olympus DP1O digital camera and customized dual port.
Temperature Dependent Equipment The temperature of all temperature-dependent equipment in the Laser Scanning Cytology Laboratory in a preferred embodiment is checked daily and recorded. Acceptable ranges may be defined for each piece of equipment, such as an acceptable refrigerator temperature range being about 2–8° C. In a specific embodiment a record of these checks may be kept.
Thermometers In a specific embodiment all thermometers in use in the Laser Scanning Cytology Laboratory are calibrated with a NIST thermometric standard thermometer before being put into use. A record of the checks can be found in the Laser Scanning Cytology Laboratory.
Maintenance In a specific embodiment electrical equipment, pipets and centrifuges are calibrated annually.
Reagents Reagents include propidium iodide solution, mouse anti-human cytokeratin-FITC, Phosphate buffered saline, and 95% ethanol.

Propidium Iodide Solution

In a preferred embodiment 50 mg/ml propidium iodide (Sigma Chemical Co.) and 200 µg/ml RNase Type 11 A Bovine (Sigma Chemical Co.) are dissolved in PBS. When stored at 4 C and protected from light, the reagent is stable for 3 months. Propidium iodide is handled with care to avoid direct contact with skin or mucous membranes as propidium iodide may cause heritable genetic damage.

Mouse Anti-Human Cytokeratin-FITC

A solution of FITC-conjugated anti-cytokeratin antibody (CK antibody) contains a ratio of 1:50 in PBS.
Supplies Supplies include the following: silane-coated microscopic slides, coverslips, 18×18×1, pipet-tips (1–200 uL), disposable transfer pipets, coplin jars, gauze, permanent marker, moist chamber, rubber cement and a urologic cytology kit.

In a specific embodiment controls are used, such as Flow-check Fluorospheres (Coulter Corp) or Rainbow Particles (Spherotech)

Example 4

Procedures for LSC Methods

Sample

The types of specimens analyzed for DNA by the Laser Scanning Cytology Laboratory are samples from patients having either a history of previous transitional cell carcinoma (TCC) or currently having a high risk for TCC. A 100-mL sample of urine mixed with an equal volume of 50% ethanol is used.
Specimen Handling All specimens are treated as biohazardous or infectious materials. The use of universal precautions during the processing of specimens and staining of slides is essential.
Cytospin Protocol for Preparation of Slides The cell concentration of the specimen is brought to $50 \times 10^3$/ml. The silane-coated slide is labeled with an identifier number. For specimens other than that of the patient, the slide is labeled with sample type and date. The slide, metal clip, filter, and sample chamber(s) of the cytospin are assembled and loaded into the chambers of the cytospin, making sure the instrument remains balanced. Then, approximately 200 ml of specimen is added to each chamber and spun at about 400 RPM for approximately 4 minutes. The slide is quickly removed without disturbing the button and then is immersed in 95% ethanol to fix the cells. Slides may remain immersed in the 95% ethanol fixative in the refrigerator until further processing, assuming that processing will occur within the next five days. If processing is to be delayed for more than 5 days, the slides can be removed from the ethanol after a minimum of about 10 minutes, air-dried, and frozen at –80° C.
Staining of Epithelial Cells for DNA Content Cytospin slides are immediately fixed in 95% ethanol, rinsed in PBS several times for about five minutes each, and placed into a moist chamber. Next, approximately 20 µl per slide of mouse anti-human cytokeratin monoclonal antibody that is conjugated with FITC (anti-CK FITC) is added to cover the spot of fixed cells on the slide, and the slide is then incubated in a moist chamber at room temperature for about 30 minutes. The slide is then rinsed with phosphate buffered saline (PBS) about 3 times, each time for about 3 minutes, followed by addition of about 20 µl of Propidium Iodide Staining Solution to cover the entire spot of cells on slide. A coverslip is added, and the edges are sealed with rubber cement. The slide is then left in the dark for about 15 minutes, followed by analysis on the LSC.
Integration of DNA Content and Cytology The identification of epithelial cells on a slide with a specific DNA content can be achieved immediately after scanning by allowing the LSC software to relocate individual epithelial cells of interest. The use of dual-color fluorescent staining provides the ability to identify morphology. In addition, slides are subsequently Pap stained and the cells are again relocated for final evaluation.

Pap Stain

Immediately after the slides have been scanned for DNA content, the rubber cement from the edges of the coverslip is carefully removed and the slide is immersed in PBS. The coverslip can be removed easily from the slide; however, there are times when the slide will require some time to soak in the PBS before the coverslip can be removed. The slide is rinsed in PBS and allowed to air-dry, followed by rinsing in a running tap water bath for about 1 minute. Afterwards, the slide is placed in a hematoxylin solution for about 25 seconds, followed by a rinse in running tap water until it is clear. The slide is quickly dipped once in HCl, followed by another rinse in running tap water for about one minute. Afterwards, the slide is dipped about 10 times in 95% ethanol, about three times in Orange-G stain, and about 10 times in 95% ethanol. This is repeated in a fresh bath of 95% ethanol. The slide is then immersed in EA for about 4.5 minutes, dipped about 10 times in 95% ethanol, dipped about 10 times in 95% ethanol, dipped about 10 times in 100% ethanol, and dipped about 10 times in a second coplin jar of 100% ethanol. The slide is then placed in two consecutive xylene baths for about 1 minute each. Finally, a coverslip is placed on the slide.

Example 5

Operating the Laser Scanning Cytometer

LSC Start Up

The microscope is uncovered and the Laser Power and Main Power are turned on.

Laser Safety Precautions

The laser contained in the LSC is a Class 1 Laser Product that complies with DHHS radiation performance standards 21 CFR Chapter 1, Subchapter S. Under no circumstances should one stare into its beam. The laser beam is visible when the cover is removed. Under no circumstance should an untrained operator remove the cover to the laser beam. The PC and its auxiliaries are turned on with the main switch. If epi-fluorescence is needed, the Olympus mercury burner is turned on.

Opening Software

The WinCyte icon is selected, which will return the stage to its "home" position. A cytometer log-in dialog box will appear. The "OK" for Alpha/Beta." button is selected. The report mode is not selected. The X and Y coordinates are verified to both be "0", the home position.

Example 6

Data Acquisition

Flow-Check Fluorospheres

The slide is removed from the refrigerator and given enough time for condensation to evaporate. Depending on the sample type, the corresponding Pro. and Dpr. Files are opened. For example, to analyze Flow-Check Fluorospheres, the Check Beads.pro and Check Beads.dpr files are opened. The "Load Slide" button is clicked, and the slide is placed on the stage with the label end on the right. For Epi-fluorescence, the "WIB" filter is selected. The Light Path Selector Knob is pulled out, and the scan area is set by clicking on "Scan Area" on the menu bar.

Using the arrow buttons on the coarse stage positioning control pad, the stage is moved to position the slide in the top right position to a beginning point for scanning. The image is focused as needed on the front CCD camera or through the oculars. The button "Top right" is selected in the scan area dialog box when the slide is in the desired position. In the same way, the stage is moved to position the slide in the bottom left position to complete the scan, and the "Bottom left" in the scan area dialog box is selected. The "Add Scan Area" is subsequently selected, followed by selection of "Stop on max total count of 1000" and "Calculate Y Step." Then, the "OK" button is selected to close the scan area dialog box, or the "Go" button is selected to begin scanning. The "Sensors" on the Menu Bar to open the sensor settings dialog box. The activated PMTs are displayed with each offset and gain. The offset distance is roughly 2 mm and is usually set to 2100. The color bar comes out to about ¾ the length of the full distance. The full distance indicates saturation, a condition that should be avoided. The filter disk is turned to the blank "0" setting, followed by pushing in of the light path selector knob. The focusing knob is adjusted to focus on the back CCD camera, and the "Go" button on the menu bar is selected to begin scanning. As the images pass on the back camera, the microscope is focused as needed. The offset distance is checked, the PMT intensities are monitored, and both are adjusted as needed. If the gain is changed during scanning, then the "Apply" button is selected in the Sensor Setting window. It is important to note that when scanning Flow-Check Fluorospheres, gain is set per lot number. It is set only the first time the lot is scanned; subsequently, gains remain constant and the PMT means are monitored for fluctuations.

Separate events from background are subject to threshold such that all cells of interest should be contoured while background fluorescence should not. The button "Scan Data Display" is selected to check contours (this can be done only while the LSC is scanning). The Red parameter in the list box for contouring is selected, and this must also be selected in the menu Instrument Settings under Computations. The contours box to display the Threshold data. By selecting the "Magnify" or "Condense" buttons, the image may be increased or reduced in size. Selecting "Next" advances the display to the next field scanned.

The cell density on the slide determines the appropriate threshold value. The correct value is successfully reached through trial and error. Generally, the value immediately inside the green contour (between the red and green bands) should be 1.5 to 2 times the background value. When the majority of cells are not touching and the signals are well above background noise, a value of 2000 usually provides good contouring. When contours are set, the image screen is closed and the data is collected. As soon as data collection is completed, the information must be saved as a FCS file in the Flow-Check Fluorospheres folder.

Example 7

Analysis of Data

On the first scattergram, Red Max Pixel Vs Area, scale factor for the X-axis is always set on 82. A region is drawn around the group of single cells or beads. A histogram for each fluorescence integral is gated from the region of interest selected from the first scattergram. The region statistics for each histogram is displayed, being sure to check the values for MCF and FWHM. The MCF values must fall within 3 standard deviations of the average mean value. This value is calculated from the first 20 scans of the new lot of beads and is applied for the life of that lot. FWHM must be less than or equal to about 5%. These values are recorded on the corresponding table. A report is printed with the above histograms and region statistics, and filed in a Flow-Check Fluorospheres binder.

Urine Specimens

Urine samples are analyzed in the same manner as the Flow-Check Fluorospheres with the following modifications. The files Swanson.pro and Swanson.dpr are opened. Epithelial cells in the urine samples are identified by their reactivity with anti-cytokeratin monoclonal antibody. A gate on cytokeratin-positive cells is set, and a minimum of about 100 cytokeratin-positive cells is required for analysis. The display is then saved in a file labeled with the patient's identifier number. The data is saved in a file labeled with the patient's identifier number.

Data Analysis

On the Ungated DNA Histogram, the diploid peak is highlighted by dragging the mouse over the area, and once the peak is highlighted, the button "Set DI" is selected. The "Set DI Index" window appears to designate the type of cells, and the "Human (100%)" button is highlighted and selected. The display properties are selected on the ungated histogram, followed by selection of the "Normalize" and "OK" buttons to replay the data. The "Tag DI" button is selected, and the histogram of interest for labeling of the DI is selected. The tag can be moved once it is placed on the graph by dragging. Regions are placed so that Diploid (2c), Tetraploid (>2c–4c), and Aneuploid (>5c) populations are defined. A criteria for acceptability of histograms is that only cytokeratin-positive cells are included. Cells within each region of the histogram are relocated to determine whether the DNA content is representative of singlets, doublets, or triplets. Only the DNA content of single cells is included within each region. DNA content of doublets and triplets are excluded from the analysis. The display and data are then saved in a file labeled with a patient identifier number, and a report page for the file is printed.

Relocating Scanned Cells

Once the data has been collected by scanning the slide, the data is ready to be analyzed with the aid of relocating the fluorescent and Papanicolaou-stained cells. Relocation confirms that the population consists of single cells and not doublets in addition to providing correlation between cell morphology and DNA ploidy. Relocation of fluorescent cells requires the use of the Epi light while relocation of Pap-stained cells requires the use of brightfield. Otherwise, the procedure that follows for Papanicolaou-stained cells is the same for both.

The fcs and dpr files for the slide are opened, and the Pap-stained slide is placed on the microscope stage in the same orientation as it was previously scanned for DNA. Regions around the populations of interest for relocation are created. In the control panel under "Display Settings", the desktop area 1024×768 is selected. The Brightfield button is selected followed by selection of the window containing the region of interest, the icon to view cells in region and the region to be relocated. The button "View Cells Using CCD Camera" is selected, followed by selection of the "Create Cell Features" window, and options to customize the table of features of a given cell event. The button "Visualize Temporary Offset" is selected if needed, and the "Icon" button is selected to reread the data. The "Green Forward Arrow" icon is selected to advance to each event. The region on the Red Max Pixel Vs Area scattergram is adjusted as needed to only include single-cell events. The Red Max Pixel Vs Area scattergram may have a population of dead/degenerated cells that will typically be located in the bottom left region of the graph. These cells are excluded from the analysis during relocation.

Collecting Cell Images

As the relocation process occurs, representative images of the slide are digitally recorded for documentation and integration into the final report. The Digital Camera Memory Card is inserted into the Olympus DP10 Camera, and the power button is pushed. The two light path selector knobs to the first notch are pushed. When an image appears on the screen that should be recorded, that same image on the digital camera screen is viewed, bringing it into focus as necessary. The lamp power is adjusted slightly to avoid underexposure. Next, on the Olympus camera control panel the record mode is selected, followed by selection of the button "Expose". The digital image for the event is recorded. This is repeated until a sufficient number of events is recorded.

Transferring Images into ImageQuest

The memory card is removed from the camera and inserted into the external drive. The ImageQuest software is opened and logged onto. The appropriate server cabinet is selected and the button "New" is selected. The case information is entered as prompted and saved. The image menu and select import images are selected. The removable Disk F is opened, followed by opening of the file "Imolym." The desired images are highlightted and the button "Open." is selected.

The image is then highlighted and exported, followed by saving of the image in a folder in the drive C. This is repeated for each image.

Editing Images

The program ImageQuest is closed, and the program Paint Shop Pro is opened. Each image is imported from the drive C and reduced as needed. The image is then cropped to focus on the cell of interest. The brightness/contrast, highlight/midtone/shadow and luminance parameters are adjusted as necessary. A border is then added to the image, followed by addition of the text "cytologic features" to the bottom of the image. The edited images are then saved in a case file labeled with the appropriate patient identifier label in the C drive.

Saving DNA Ploidy Histogram

Once the DNA Histogram is finalized, the graph is copied and pasted into Paint Shop Pro. In Paint Shop Pro, the file "axis" is opened, and the image is pasted along the x axis of the DNA Histogram. A border is added to the histogram, which is then saved to a disk. The file is then transferred to the main patient file in the C drive on the Compaq PC.

Example 8

Clinical Interpretation

The cytopathologist or one skilled in the art provides clinical interpretation. A population containing more than about 5% of cells >about 5 c may be of clinical importance. Data on the percentages of cells that are diploid, tetraploid and aneuploid are provided to the cytopathologist who integrates these data with cytologic findings to issue a report. A draft report is prepared containing the ploidy analysis and histogram and submitted along with the Pap-stained slide to a cytopathologist or skilled artisan for clinical interpretation.

Creating Longitudinal Patient History Graph

The LSC Long Rpt is opened on the desktop. The graph is selected to get the datasheet, and the appropriate file identifier numbers are entered. The datasheet is closed, and the outside of the graph is selected to see the completed graph. All of the data is selected and cut and pasted into Paint Shop Pro. The image size is reduced, cropped, and have a border added to it as needed. The file is then saved with the appropriate file identifier numbers in the C drive.

Creating Final Report

The report template is opened in Microsoft Word, and the appropriate patient identifier number is entered in the top portion of the report. The morphologic diagnosis as verified by the Cytopathologist is entered. In the comment section, the ploidy analysis as verified by the Cytopathologist is entered. The Cytologic Findings Image box is selected, and the image is inserted, as selected by the cytopathologist, from the patient file. The size is adjusted as needed. The DNA Content Image box is selected, and the DNA histogram from the patient file is selected. The size as adjusted as needed. The longitudinal analysis box is selected and the longitudinal graph is inserted. The size is adjusted as needed. The Final Diagnostic Category box is selected, and the date is entered, the file is saved, and the data is printed and submitted for a cytopathologist's signature.

Shut Down

All desired changes to the dpr file are saved. The WinCyte program is saved. The buttons "Start," "Shut Down," and "Yes" are selected. When prompted, the computer and accessories are shut down with the main switch. The laser is switched off, as is the main power of the LSC.

Example 9

Data Storage/Archiving

Data Storage on PC

Each case consists of several digital images of cells, a DNA histogran, a longitudinal report and a final report. This set of data is saved in a file labeled with the accession number and patient hospital number. The file in (#1) is saved in a patient file containing repeat patient cases. This file is labeled with the patient hospital number only. The file in (#2) is saved in the LSC MDACC directory located on the Drive C of the PC. This directory contains all patient files. Periodically, patient files will be transferred to optical disk drives for backup storage.

Data Storage on LSC

In the WinCyte software, which is in the Drive C in the Cyte directory, each scanned slide is saved in the Alpha/Beta directory. Each scanned slide has a FCS and a DPR file labeled with the patient hospital number. In the case of a repeat patient, the hospital number is followed with a, b, c, etc. At the time of saving the fcs file, a comment box appears in which the accession number and sample type are entered and saved as part of the file.

Example 10

Quality Control

Criteria for Rejecting Specimens

A minimum of 100 cytokeratin-positive cells per slide is required for reliable DNA ploidy analysis. This condition does not preclude the analysis for cytology.

Daily and Monthly Controls

Appropriate control specimens will be run daily when samples are processed to ensure that staining and instrumentation are performing properly. Flow-Check Fluorospheres purchased from Coulter Corporation will be run daily to monitor linearity and DNA ploidy. Rainbow Particles are scanned monthly to establish consistency in mean channel fluorescence (MCF) and alignment.

Flow-Check Fluorospheres (Daily)

When opening a new bottle, the solution is concentrated by siphoning off half of the liquid when the beads are settled at the bottom. Every time a slide is made, the concentrated solution well is vortexed. One drop is placed straight from the bottle onto the slide. A 18×18 mm coverslip is placed, blotted and the edges are sealed with clear nail polish. The slide is placed in the refrigerator for about 5 minutes while the beads settle on the slide. The Flow-Check Fluorospheres are checked according to the procedure outlined herein. When stored refrigerated in the dark, the Flow-Check Fluorospheres slide should last at least a week.

Rainbow Particles (Monthly)

Rainbow Particles are used to evaluate the alignment and PMT of the Laser Scanning Cytometer. These particles have a wide spectrum of fluorescence intensities and will show signals up to 7 decades of log intensities. A Rainbow Particles slide is scanned once a month. The concentrated particles are kept available, one ml from the bottle is centrifuged, and about 0.5 ml of the supernatant is removed.

The vial is marked with the date prepared and stored in the refrigerator in the dark. The concentrated solution is vortexed well every time a slide is prepared. Twenty $\mu$L of solution is placed onto the slide and covered with a 18×18 mm coverslip, blotted and sealed with clear nail polish. The slide is placed in the refrigerator for about five minutes to allow the beads to settle. The slide is then scanned according to the procedures described herein.

Biological Controls

A biological control slide is stained with every batch of specimen slides. It is scanned and used for setting the DI (DNA Index). In a specific embodiment the cells are of epithelial origin to provide a check for anti-cytokeratin antibody positivity when examining a urine sample for transitional cell carcinoma. In another embodiment the cell lines to be used are HeLa cells and UC3 Bladder cells.

Example 11

Tolerance

Out-Of-Limits Condition

A method or instrument may be out of limits and if corrective action is needed if the Flow-Check Fluorospheres result is more than three standard deviations from the mean, if two consecutive control results are more than two standard deviations from the mean and/or if the coefficient of variation FWHM is > about 5%.

Corrective Action

The existence of an out-of-limits condition indicates only that there is the possibility that a problem exists with an instrument or method. Repeat analysis of the controls may be all that is needed to confirm that there is no problem. If it is determined a problem exists, the progressive actions taken will involve: (1) rescan the slide in the same area, ensuring that the slide is in focus; rescan the same slide in a different area; scan a freshly made slide; or scan a test slide of known ploidy. If both mean and FWHM are out of range, alignment may be the source of the problem. However, if only FWHM goes up, then it is probably an alignment issue. If only the mean is out of range and FWHM looks satisfactory, it might indicate a PMT problem. The PMT could be aging and may require more strength. If this is the case, the gain setting may be increased.

Example 12

Documentation

In addition to entering the quality control values themselves, a log is maintained with one entry for each out-of-limits condition stating what was done in response to the condition. If no action was necessary and analysis continued, then this is documented. Finally, significant events (new reagent lots, instrument maintenance, etc.) are noted, so that they can be correlated with any changes in the quality control, should that occur. It is preferred to use reagents which are not beyond any expiration date for use.

Example 13

Reagent Validation

Validation of Antibodies

In the event that reagents are aliquoted and stored frozen, they may be used even if past the stated expiration date provided that the activity of such reagents has been checked against an aliquot in current use and the results documented.

New Antibodies

Newly received antibodies must be dated, initialed and stored according to manufacturer's recommendation. Typically, reagents are stored at about 4 C. In addition, the activity of newly received antibodies must be validated prior to clinical usage. This is accomplished simply by: 1) testing the new antibody on one or more clinical specimens known to be positive for the antigen against which the antibody is directed; 2) comparing these results with those of old antibodies of proven activity on the same clinical specimen (s); and/or 3) obtain and print uncompensated and compensated scattergrams comparing the old and new antibodies.

The appropriate fluorescent channel of the new and old scattergrams should match with respect to mean intensity and percent positivity within 10%. If so, the new antibody can be recorded on the corresponding quality control sheet as having been validated for clinical usage and may be so utilized. If not, the new antibody is not validated and may not be utilized without explicit permission from the pathologist or laboratory director and a note to this effect must be entered on the quality control sheet.

Expired (Out of Date) Antibodies

Expired antibodies may still be used, but only if their activity is closely monitored and validated on a monthly basis. This is accomplished by frequently documenting the activity of such antibodies on clinical specimens known to be positive for the corresponding antigens based on patterns of antigenicity within the specimens. Additionally, the intensity of reactivity and fluorescence must also be monitored frequently and compared with that of positive clinical specimens throughout the usage of the antibody. In order to maintain their validation for clinical usage, appropriate positive and negative results (with respect to percent positivity and fluorescent intensity) on at least one clinical specimen must be documented. Expired antibodies not so validated may not be used clinically.

Example 14

Reporting

Detection of Clerical Errors, Significant Analytical Errors, and Unusual Laboratory Results Despite the use of statistical quality control procedures at the time of analysis, there are still a variety of opportunities for incorrect results to be inadvertently generated. Therefore the following procedures will be used to detect these errors as soon as possible, preferably before the results are posted to the patient's chart.

Any result for which there is any doubt for any reason must be repeated using a new specimen. If there is any question whatever of the identity or correct handling of a specimen, then a new specimen should be requested. Before accepting results into the computer system, previous results should be reviewed by the technologist and compared with the results being entered. Any unexplainable discrepancies are reported to the pathologist and, if necessary, the appropriate procedure for correcting the results is followed before the results are verified. Frequently, about 5% of all released reports will be retrieved at random and reviewed for clerical or other errors. If clerical errors or other discrepancies are discovered upon review of a released report, then a second report containing the necessary corrections will be issued and noted as revised.

Example 15

Quality Assurance

DNA Ploidy

To monitor quality assurance of the DNA Ploidy, parallel testing of split samples is performed with other techniques known in the art. Whereas DNA content is assessed by staining the cells with propidium iodide and analyzed on laser-based technology for LSC, alternative methods may include those such as the staining of cell nuclei with Feulgen's stain and determination of the DNA content on a system that is not laser-based.

Quality Improvement

The Quality Improvement program for DNA Ploidy analysis includes frequent meetings to improve such parameters as turn around time, internal controls for ploidy and isotype controls for immunofluorescence, such as cytokeratin.

References

One skilled in the art readily appreciates that the present invention is well adapted to carry out the objectives and obtain the ends and advantages mentioned as well as those inherent therein. Methods, compositions, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

| U.S. Pat. No. 5,427,910 | Kamentsky et al. | Jun. 27, 1995 |
| U.S. Pat. No. 5,793,969 | Kamentsky et al. | Aug. 11, 1998 |
| U.S. Pat. No. 5,885,840 | Kamentsky et al. | Mar. 23, 1999 |

Publications

Batsakis J G, Sneige N, el-Naggar AK. Flow cytometric (DNA content and S-phase fraction) analysis of breast cancer. Cancer 1993;71:2151–2153.

Bedrossian, C W M. Special stains, the old and the new: the impact of immunocytochemistry in effusion cytology. Diagnostic Cytopathology 1998; 18(2):141–149.

Clatch R J, Walloch J L, Zufter M M, Kamentsky L A. Immunophenotypic analysis of hematologic malignancy by laser scanning cytometry. Am J Clin Pathol 1996:105:744–755.

Clatch, Richard J.. Walloch. Jami L., Foreman, James R., and Kamentsky, Louis A. Multiparameter analysis of DNA content and cytokeratin expression in breast carcinoma by laser scanning cytometry. Arch Pathol Lab Med. 1997 Jun;121(6):585–92.

Coon J S, Weinstein R S. Diagnostic flow cytometry. Baltimore: Williams & Wilkins, 1991.

Hedley D W. DNA Cytometry Consensus Conference. DNA flow cytometry and breast cancer. Breast Cancer Res Treat 1993:28:51–53.

Huffinan J L, Garin-Chesa P, Gay H, Whitmore W F Jr, Melamed M. Flow cytometric identification of human bladder cells using a cytokeratin monoclonal antibody. Ann NY Acad Sci 1986;468:302–31 S.

Kamentsky L A, Kamentsky L D. Microscope-based multiparameter laser scanning cytometer yielding data comparable to flow cytometry data. Cytometry 1991;12:381–387.

Keren O F, Hanson C A, Hurtubise P E. Flow cytometry and clinical diagnosis. Chicago: ASCP Press, 1993.

Krishan A: Rapid flow cytofluorometric analysis of mammalian cell cycle by propidium iodide. J. Cell Siol. 66: 188–197.

Martin-Reay O G. Kamentsky L A, Weinberg O S, Hollister K A, Cibas E S. Evaluation of a new slide-based laser scanning cytometer for DNA analysis of tumors. Comparison with flow cytometry and image analysis. Am J Clin Pathol 1994;102:432–438.

Park C H, Kimier S F. Tumor cell-selective flow cytometric analysis for DNA content and cytokeratin expression of clinical tumor specimens by "cross-gating". Anticancer Res 1994;14:29–36.

Sasaki K, Kurose A, Miura Y, Sato T, Ikeda E. DNA ploidy analysis by laser scanning cytometry (LSC) in colorectal cancers and comparison with flow cytometry. Cytometry 1996;23:106–109.

Sauer K D, Duque R E, Shankey T V. Clinical flow cytometry. Baltimore: Williams & Wilkins, 1993.

Spyratos F. DNA content and cell cycle analysis by flow cytometry in clinical samples: application in breast cancer. Biol Cell 1993;78:69–72.

Visscher O W, Zarbo R J, Sakr W A, Crissman J D. Flow cytometric DNA and cell cycle analysis of cytokeratin-labeled breast carcinomas: Correlations with prognostic factors. Lab Invest 1989;60:102A.

Wingren S, Stal O, Nordenskjold S. Flow cytometric analysis of S-phase fraction in breast carcinomas using gating on cells containing cytokeratin. Eur J Cancer 1994;69:546–549.

What is claimed:

1. A method for recording cell sample data comprising:
   (a) providing a sample containing a cell;
   (b) subjecting said sample to a laser-based interrogation; and
   (c) directly capturing a digital image of one or more cell characteristics.

2. The method of claim 1, further comprising analyzing said one or more cell characteristics.

3. The method of claim 2, further comprising analyzing said one or more cell characteristics by fluorescent in situ hybridization.

4. The method of claim 2, wherein said one or more cell characteristics are selected from the group consisting of immunophenotype, DNA ploidy, cell morphology, nuclear fragments and subcellular fragments.

5. The method of claim 1, wherein said one or more cell characteristics comprises immunophenotype, DNA ploidy, cell morphology, nuclear fragments and subcellular fragments.

6. The method of claim 1, wherein said cell is selected from the group consisting of an animal cell, a plant cell and a prokaryotic cell.

7. The method of claim 6, wherein said animal cell is selected from the group consisting of a cancer cell, an epithelial cell, a bone marrow cell, a red blood cell, a white blood cell, a muscle cell, a bone cell, a connective tissue cell, a nerve cell and a brain cell.

8. The method of claim 1, wherein said cell is a cancer cell.

9. The method of claim 1, further comprising the step of preparing a cell sample.

10. The method of claim 9, wherein the preparation step comprises processing of a sample, wherein said sample processing is selected from the group consisting of concentration, dilution, microscope analysis preparation, applying a stain or marker agent, or a combination thereof.

11. The method of claim 1, wherein said sample is selected from the group consisting of urine, blood, sputum, feces, saliva, marrow, touch preps of surgical specimens, lymph nodes, fine needle aspirates and cellular body fluid.

12. The method of claim 1, further comprising capturing a video image of said cell sample.

13. The method of claim 1, further comprising capturing a color image of said cell sample.

14. The method of claim 1, further comprising capturing a black and white image of said cell sample.

15. The method of claim 10, wherein said marker agent is selected from the group consisting of cytokeratin, propidium iodide, CD19, CD34, CD3, annexin V, and a combination thereof.

16. The method of claim 5, wherein said DNA ploidy of said cell is aneuploid.

17. The method of claim 5, wherein said one or more cell characteristics are analyzed from the same said digital image.

18. The method of claim 4, wherein said immunophenotype is determined by applying a marker agent.

19. The method of claim 18, wherein said marker agent is selected from the group consisting of cytokeratin, propidium iodide, CD19, CD34, CD3, annexin V, and a combination thereof.

20. The method of claim 18, wherein said immunophenotype is determined by applying multiple marker agents.

21. A method of diagnosing cancer comprising:
   (a) providing a sample containing a cell;
   (b) subjecting said sample to a laser-based interrogation;
   (c) directly capturing a digital image of one or more cell characteristics; and
   (d) identifying aneuploidy based on said one or more cell characteristics.

22. A method for creating a cell data record comprising:
   (a) subjecting a cell to laser interrogation; and
   (b) directly recording in a tangible medium one or more cell characteristics in a digital format.

23. A method for recording cell sample data comprising:
   (a) providing a sample containing a cell;
   (b) subjecting said sample to a laser-based interrogation; and
   (c) capturing by digital camera a digital image of one or more cell characteristics.

24. The method of claim 23, wherein said digital image is directly captured.

25. The method of claim 23, further comprising analyzing said one or more cell characteristics.

26. The method of claim 25, further comprising analyzing said one or more cell characteristics by fluorescent in situ hybridization.

27. The method of claim 25, wherein said one or more cell characteristics are selected from the group consisting of immunophenotype, DNA ploidy, cell morphology, nuclear fragments and subcellular fragments.

28. The method of claim 23, wherein said one or more cell characteristics comprises inmmunophenotype, DNA ploidy, cell morphology, nuclear fragments and subcellular fragments.

29. The method of claim 23, wherein said cell is selected from the group consisting of an animal cell, a plant cell and a prokaryotic cell.

30. The method of claim 29, wherein said animal cell is selected from the group consisting of a cancer cell, an epithelial cell, a bone marrow cell, a red blood cell, a white blood cell, a muscle cell, a bone cell, a connective tissue cell, a nerve cell and a brain cell.

31. The method of claim 23, wherein said cell is a cancer cell.

32. The method of claim 23, further comprising the step of preparing a cell sample.

33. The method of claim 32, wherein the preparation step comprises processing of a sample, wherein said sample processing is selected from the group consisting of concentration, dilution, microscope analysis preparation, applying a stain or marker agent, or a combination thereof.

34. The method of claim 33, wherein said sample is selected from the group consisting of urine, blood, sputum, feces, saliva, marrow, touch preps of surgical specimens, lymph nodes, fine needle aspirates and cellular body fluid.

35. The method of claim 33, further comprising capturing a video image of said cell sample.

36. The method of claim 33, further comprising capturing a color image of said cell sample.

37. The method of claim 33, further comprising capturing a black and white image of said cell sample.

38. The method of claim 37, wherein said marker agent is selected from the group consisting of cytokeratin, propidium iodide, CD19, CD34, CD3, annexin V, and a combination thereof.

39. The method of claim 38, wherein said DNA ploidy of said cell is aneuploid.

40. The method of claim 38, wherein said one or more cell characteristics are analyzed from the same said digital image.

41. The method of claim 37, wherein said immunophenotype is determined by applying a marker agent.

42. The method of claim 41, wherein said marker agent is selected from the group consisting of cytokeratin, propidium iodide, CD19, CD34, CD3, annexin V, and a combination thereof.

43. The method of claim 41, wherein said immunophenotype is determined by applying multiple marker agents.

44. A method of diagnosing cancer comprising:
  (a) providing a sample containing a cell;
  (b) subjecting said sample to a laser-based interrogation;
  (c) capturing by digital camera a digital image of one or more cell characteristics; and
  (d) identifying aneuploidy based on said one or more cell characteristics.

45. A method for creating a cell data record comprising:
  (a) subjecting a cell to laser interrogation; and
  (b) recording by a digital camera one or more cell characteristics in a digital format.

* * * * *